United States Patent
Shin et al.

(10) Patent No.: US 9,416,122 B2
(45) Date of Patent: Aug. 16, 2016

(54) HIGH REFRACTIVE (METH)ACRYLATE DERIVATIVE AND METHOD FOR PREPARING THE SAME

(71) Applicant: Daelim Chemical Co., Ltd, Gyeong-sangnam-do (KR)

(72) Inventors: Hong Hyun Shin, Seoul (KR); Ssang Soo Han, Gyeonggi-do (KR); Chun Ho Kong, Gyeongsangnam-do (KR); Gyeong Hyeon Gim, Gyeongsangnam-do (KR)

(73) Assignee: DAELIM CHEMICAL CO., LTD., Gyeong-Sangnam-Do (KR)

( * ) Notice: Subject to any disclaimer, the term of this patent is extended or adjusted under 35 U.S.C. 154(b) by 0 days.

(21) Appl. No.: 14/432,702

(22) PCT Filed: Jul. 23, 2013

(86) PCT No.: PCT/KR2013/006573
§ 371 (c)(1),
(2) Date: Mar. 31, 2015

(87) PCT Pub. No.: WO2014/104513
PCT Pub. Date: Jul. 3, 2014

(65) Prior Publication Data
US 2015/0225364 A1  Aug. 13, 2015

(30) Foreign Application Priority Data

Dec. 28, 2012 (KR) .................. 10-2012-0156547

(51) Int. Cl.
C07D 333/76 (2006.01)
C07D 307/91 (2006.01)
G02B 5/04 (2006.01)
G02B 1/04 (2006.01)

(52) U.S. Cl.
CPC ............ C07D 333/76 (2013.01); C07D 307/91 (2013.01); G02B 5/04 (2013.01); G02B 1/041 (2013.01)

(58) Field of Classification Search
CPC ...................................... C07D 333/76
USPC ........................................... 549/43
See application file for complete search history.

(56) References Cited

U.S. PATENT DOCUMENTS 5,932,626 A    8/1999  Fong et al.

FOREIGN PATENT DOCUMENTS

| KR | 10-0658513 B1 | 12/2006 |
|---|---|---|
| KR | 10-2010-0070110 A | 6/2010 |
| SU | 759530 A1 | 8/1980 |
| SU | 763342 A1 * | 9/1980 |
| WO | WO-2013-011893 A1 | 1/2013 |

OTHER PUBLICATIONS

International Search Report in International Application No. PCT/KR2013/006573, filed Jul. 23, 2013.
Office Action dated Dec. 22, 2015 in Chinese Application No. 201380050079.2.
Dongsheng, Review of Chloromethylation Methods, Nov. 3, 1999, pp. 229-234, vol. 11, No. 3, Xiangtan, Hunan.

* cited by examiner

*Primary Examiner* — Taofiq A Solola
(74) *Attorney, Agent, or Firm* — Saliwanchik, Lloyd & Eisenschenk

(57) ABSTRACT

Provided are a high refractive (meth)acrylate derivative and a method or preparing the same, and more particularly, a novel high refractive (meth)acrylate derivative having a high refractive index, capable of being used in a display component material such as an optical film, and a method for preparing the same.

6 Claims, No Drawings

HIGH REFRACTIVE (METH)ACRYLATE DERIVATIVE AND METHOD FOR PREPARING THE SAME

CROSS-REFERENCE TO RELATED APPLICATIONS

This application is the U.S. national stage application of International Patent Application No. PCT/KR2013/006573, filed Jul. 23, 2013, which claims priority to Korean Application No. 10-2012-0156547, filed Dec. 28, 2012 the disclosure of which is hereby incorporated by reference in its entirety.

TECHNICAL FIELD

The present invention relates to a high refractive (meth)acrylate(meth)acrylate derivative and a method for preparing the same, and more particularly, to a novel high refractive (meth)acrylate derivative having a high refractive index, capable of being used in a display component material such as an optical film, and a method for preparing the same.

BACKGROUND ART

A (meth)acrylate having a high refractive index is capable of being used in an optical product, that is, an optical lens, an optical film, an optical media, or the like. In particular, the optical film is capable of being used in a display product such as a liquid crystal display and a plasma display panel, and in particular, is used in a liquid crystal display (LCD) prism sheet, or the like, to improve brightness of a back-light unit disposed in a back side of the liquid crystal display (LCD).

One important optical variable of materials configuring a prism layer of a prism film among the optical films is a refractive index, and as the refractive index is higher, performance of the prism film is improved. As an example of the prism film having the high refractive index used in order to increase efficiency of a LCD backlight, an optical product produced by a polymerizable composition containing a brominated monomer having a high refractive index is disclosed in Korean Patent Laid-Open Publication Nos. 2001-0012340 and 10-2005-0010760. However, halogen compounds such as bromine and chlorine may increase the refractive index. However, after curing, a prepared film has an increase degree of yellowing, the increased yellowing makes the performance of the film deteriorate, and the significantly increased yellowing has an influence on a display color.

That is, currently developed high refractive acrylate contains the halogen compound to be highly toxic, and at the time of combustion, large amounts of corrosive gas are generated. In addition, since a product has a significantly high viscosity or the product is in a state of a solid, at the time of preparing a coating solution, high viscosity is maintained, such that processability thereof has a problem, and since high raw materials are used, a competitive cost is deteriorated.

Therefore, there is a need for preparing a high refractive (meth)acrylate in a liquid state, which is non-halogen and has a relatively low viscosity, by a low cost process.

DISCLOSURE OF INVENTION

Technical Problem

An object of the present invention is to provide a novel (meth)acrylate derivative in which a refractive index is high, a viscosity is low, transparency is excellent at the time of curing, a degree of yellowing is small at the time of being exposed by light in a long period of time, formability and adhesive property are excellent, and optical property is excellent.

In addition, another object of the present invention is to provide a method for preparing the high refractive (meth)acrylate derivative.

In one general aspect, there is provided a novel (meth)acrylate derivative represented by the following Chemical Formula 1:

[Chemical Formula 1]

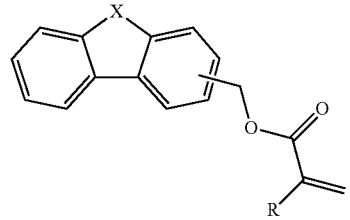

wherein X is O or S, and R is hydrogen or methyl.

The (meth)acrylate derivative may be selected from the following compounds:

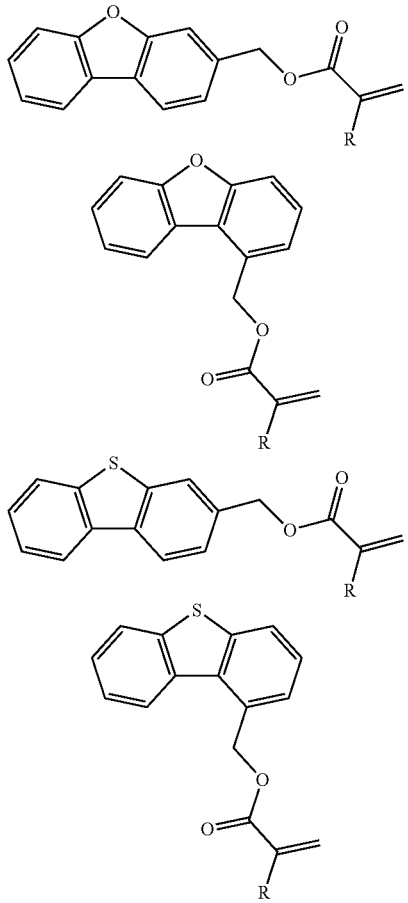

wherein R is hydrogen or methyl.

The (meth)acrylate derivative may have a viscosity of 300 to 3500 cP at 25° C. and a refractive index of 1.61 to 1.63 at 25° C.

In another general aspect, there is provided a method for preparing a high refractive (meth)acrylate derivative, the method including:

1) preparing a compound represented by the following Chemical Formula b by putting a fluorene derivative represented by the following Chemical Formula a, paraformaldehyde (PFA), and an acid into a first reactor, followed by a reaction;

2) preparing a KOH/(meth)acrylate acid aqueous solution by putting a KOH aqueous solution and a (meth)acrylic acid represented by the following Chemical Formula c into a second reactor, followed by putting Tetra-n-butylammonium bromide (TBAB) thereinto; and 3) preparing a (meth)acrylate derivative represented by the following Chemical Formula 1 by an esterification reaction of the compound represented by the following Chemical Formula b, the reaction product of the step 1), with the KOH/(meth)acrylic acid aqueous solution of the step 2):

[Chemical Formula 1]

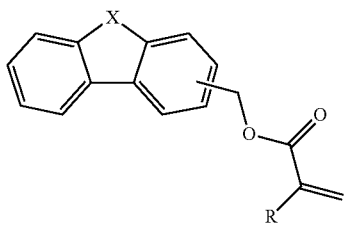

[Chemical Formula a]

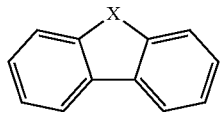

[Chemical Formula b]

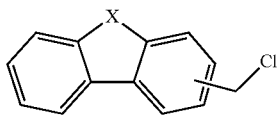

[Chemical Formula c]

wherein X is O or S, and R is hydrogen or methyl.

The acid of the step 1) may be an acetic acid, a hydrochloric acid, a phosphoric acid, a sulfuric acid, a p-toluenesulfonic acid, or a methanesulfonic acid.

A reaction temperature of the step 1) may be 80 to 85° C.

In the step 2), the putting of the KOH aqueous solution and the (meth)acrylic acid represented by Chemical Formula c into the second reactor may be performed at a temperature of 5 to 15° C. and the putting of Tetra-n-butylammonium bromide (TBAB) thereinto may be performed at a temperature of 20 to 30° C.

The esterification reaction of the step 3) may be performed at a temperature of 70 to 90° C.

The method may further include: additionally putting a polymerization inhibitor into the first reactor after performing the reaction of the step 1), or additionally putting the polymerization inhibitor after performing the esterification reaction of the step 3).

Advantageous Effects of Invention

As set forth above, the novel (meth)acrylate derivative according to the present invention, which is the liquid fluorene methyl (meth)acrylate derivative containing oxygen or sulfur at position 9 in the fluorene structure, has high refractive index and low viscosity, such that flowability and formability thereof may be superior, and the reactivity thereof may be excellent, thereby having advantages in the preparing process. In addition, the (meth)acrylate derivative is prepared by the low cost process to have economic advantages. Further, the novel (meth)acrylate derivative according to the present invention may have excellent transparency at the time of curing, small degree of yellowing even at the time of being exposed by the light in a long period of time, and excellent formability and adhesive property, and may be used in various fields such as the UV curable resin, the film, and the coating fields.

MODE FOR THE INVENTION

The present invention is to provide a high refractive (meth)acrylate derivative in a liquid state, which is represented by the following Chemical Formula 1:

[Chemical Formula 1]

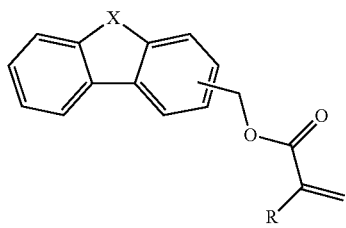

wherein X is O or S, and R is hydrogen or methyl.

The (meth)acrylate derivative according to an embodiment of the present invention may be selected from the following compounds:

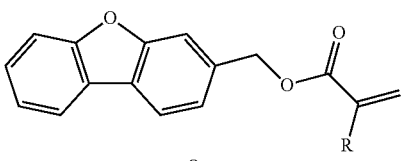

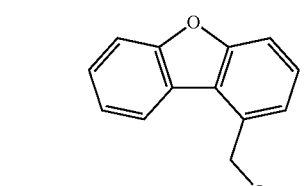

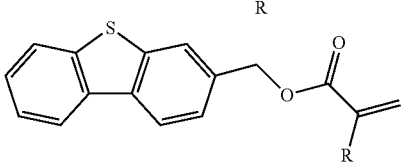

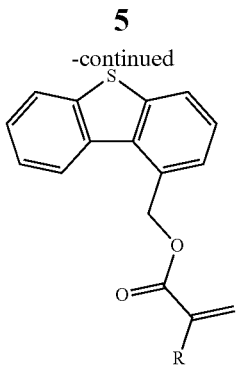

wherein R is hydrogen or methyl.

The (meth)acrylate derivative according to the embodiment of the present invention may have a viscosity of 300 to 3500 cP at 25° C. and a refractive index of 1.61 to 1.63.

In addition, the present invention is to provide a method for preparing a high refractive (meth)acrylate derivative, the method including:

1) preparing a compound represented by the following Chemical Formula b by putting a fluorene derivative represented by the following Chemical Formula a, paraformaldehyde (PFA), and an acid into a first reactor, followed by a reaction; 2) preparing a KOH/(meth)acrylic acid aqueous solution by putting a KOH aqueous solution and a (meth)acrylic acid represented by the following Chemical Formula c into a second reactor, followed by putting Tetra-n-butylammonium bromide (TBAB) thereinto; and 3) preparing a (meth)acrylate derivative represented by the following Chemical Formula 1 by an esterification reaction of the compound represented by the following Chemical Formula b, the reaction product of the step 1), with the KOH/(meth)acrylic acid aqueous solution of the step 2):

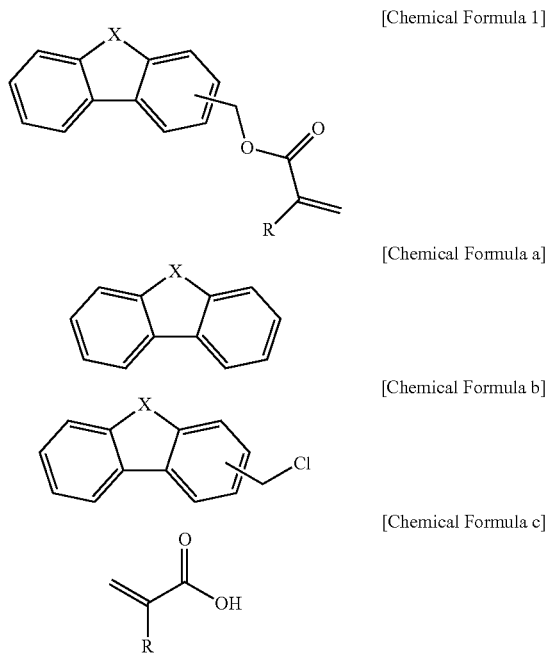

wherein X is O or S, and R is hydrogen or methyl.

Hereinafter, a method for preparing a high refractive (meth)acrylate derivative according to the embodiment of the present invention will be described in detail.

In the method for preparing the high refractive (meth)acrylate derivative according to the embodiment of the present invention, an acid of the step 1) may preferably include at least one selected from an acetic acid, a hydrochloric acid, a phosphoric acid, a sulfuric acid, a p-toluenesulfonic acid and a methanesulfonic acid, and more preferably include at least one selected from an acetic acid, a hydrochloric acid, and a phosphoric acid, but is not limited thereto.

In the method for preparing the high refractive (meth)acrylate derivative according to the embodiment of the present invention, a reaction temperature of the step 1) may be 80 to 85° C.

In the method for preparing the high refractive (meth)acrylate derivative according to the embodiment of the present invention, the KOH solution is used in order to prepare the acrylic acid of the step 2) as a salt and the same equivalent thereof is used in order to maintain the neutral pH of the solution. In addition, the putting of the KOH aqueous solution and the (meth)acrylic acid represented by Chemical Formula c into the reactor may be performed at 5 to 15° C., and the putting of Tetra-n-butylammonium bromide (TBAB), which is to smooth a reaction between a water layer and an organic layer as a phase transition catalyst, may be performed at 20 to 30° C.

In the method for preparing the high refractive (meth)acrylate derivative according to the embodiment of the present invention, an esterification reaction of the step 3) may be performed at 70 to 90° C.

In the method for preparing the high refractive (meth)acrylate derivative according to the embodiment of the present invention, a decolorization process using an activated carbon may be performed for each step in order to improve a color of the high refractive (meth)acrylate derivative which is a final product.

The method for preparing the high refractive (meth)acrylate derivative according to the embodiment of the present invention may further include: additionally putting a polymerization inhibitor into the first reactor after performing the reaction of the step 1), or additionally putting the polymerization inhibitor after performing the esterification reaction of the step 3). It is preferable that at least one polymerization inhibitor selected from a group consisting of hydroquinone, MEHQ (4-Metaoxy Phenol), tertbutylcatechol, p-benzoquinone, phenothiazine, butylated hydroxy toluene, pyrogallol, mono tertbutylhydroquinone, and di tert-butylhydroquinone is used.

In addition, the polymerization inhibitor is further added into the reactor in order to prevent the polymerization by the inner temperature of the reactor, and it is preferable that 0.04 to 0.06 parts by weight with respect to 100 parts by weight of a compound represented by Chemical Formula b after the reaction of the step 1), and 0.04 to 0.05 parts by weight with respect to 100 parts by weight of a compound represented by Chemical Formula 1 after the esterification reaction of the step 3) are used.

A (meth)acrylate compound product produced by a preparation method of the present invention may be collected by known purification method such as alkali wash, wash, distillation, filtration, and the like.

Hereinafter, the present invention will be described in detail with reference to the examples. These examples are only for exemplifying the present invention, and it will be

Example 1

Synthesis of Dibenzo[b,d]Furanylmethyl Acrylate

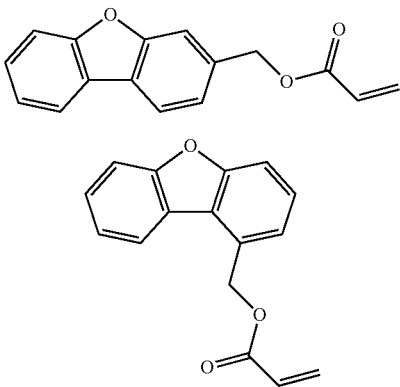

Dibenzofuran (100.0 g, 0.595 mol), paraformaldehyde (PFA) (44.6 g, 1.486 mol), distilled water (50 g) and an acetic acid (100.0 g) were put into a 1 L reactor, followed by stirring, and then a temperature was raised to 80° C. An inner temperature of the reactor was maintained at 80° C. and a HCl gas (54.2 g, 1.486 mol) was put thereinto, followed by a reaction for 5 hours. After the reaction was completed, toluene (300.0 g) was added to the reactor, and dibenzofuran having chloromethyl introduced thereinto was layer-separated as an intermediate product. The intermediate product layer was stirred, the inner temperature of the reactor was cooled to 25° C., the stirred reactant was washed and layer-separated by using refined water (200.0 g for each time) three times, and then the intermediate product layer was decolorized by using an activated carbon in order to improve a color of a final target compound. After the decolorization, the decolorized product was dehydrated by MgSO4, followed by filtration, and MEHQ (4-Metaoxy Phenol) (0.064 g, 0.00052 mol) which is a polymerization inhibitor was put into the reactant (hereinafter, referred to as a reaction solution 1).

A distilled water (200.0 g) was put into another 1 L reactor and an inner temperature of the reactor was cooled to 5° C. The inner temperature of the reactor was maintained at 15° C. or less, and 90% KOH (66.7 g, 1.070 mol) was slowly put into the reactor. After 90% KOH was completely dissolved, the inner temperature of the reactor was maintained to 15° C. or less, and an acrylic acid (85.7 g, 1.189 mol) was slowly put into the reactor. A temperature was raised to a room temperature and TBAB (Tetra-n-butylammonium bromide) (27.7 g, 0.083 mol) was put into the reactor to be dissolved, thereby preparing a KOH/AA aqueous solution.

The prepared KOH/AA aqueous solution was put into the prepared reaction solution 1 and air was injected, followed by a reaction for 4 hours at 80° C. After the reaction was completed, dibenzo[b,d]furanylmethyl acrylate was layer-separated as a final target compound, the inner temperature of the reactor was cooled to 25° C., and the reactant was washed and layer-separated by using refined water (200.0 g for each time) three times, followed by decolorization by using the activated carbon in order to improve the color of the final target compound. After the decolorization, the decolorized product was dehydrated by MgSO4, followed by filtration, and MEHQ (4-Metaoxy Phenol) (0.075 g, 0.0006 mol) which is a polymerization inhibitor was put into the reactant. A vacuum distillation device was used to distill toluene, thereby obtaining a mixture of dibenzo[b,d]furan-3-ylmethyl acrylate(A) and dibenzo[b,d]furan-1-ylmethyl acrylate(B) as the final target compound (A+B=142.2 g, yield of A+B=94.8%. A:B=1: 0.7).

1H NMR (400 MHz, CDCl3) of A: δ 5.34 (s, 2H), 5.83-5.86 (dd, 1H), 6.14-6.22 (m, 1H), 6.43-6.49 (dd, 1H), 7.31-7.35 (m, 1H), 7.43-7.48 (m, 2H), 7.53-7.58 (m, 2H), 7.90-7.97 (m, 2H)

1H NMR (400 MHz, CDCl3) of B: δ 5.32 (s, 2H), 5.83-5.86 (dd, 1H), 6.14-6.21 (m, 1H), 6.43-6.48 (dd, 1H), 7.33-7.36 (m, 1H), 7.46-7.48 (m, 2H), 7.52-7.58 (m, 2H), 7.90-7.97 (m, 2H)

Example 2

Synthesis of Dibenzo[b,d]Thiophenylmethyl Acrylate

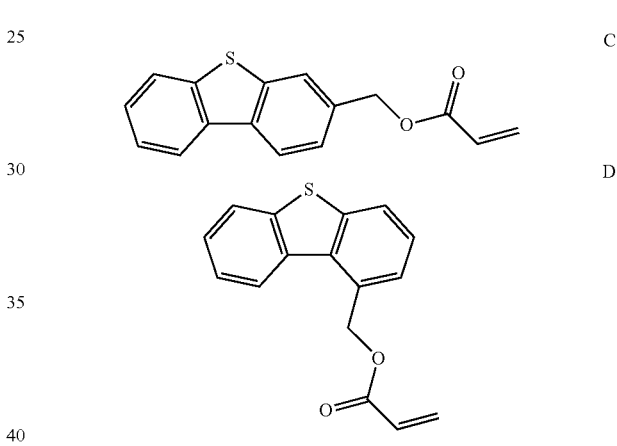

Dibenzothiophene (100.0 g, 0.543 mol), paraformaldehyde (PFA) (40.7 g, 1.357 mol), distilled water (50 g) and an acetic acid (100.0 g) were put into a L reactor, followed by stirring, and then a temperature of the reactor was raised to 90° C. An inner temperature of the reactor was maintained at 90° C., and a HCl gas (49.5 g, 1.356 mol) was put thereinto, followed by a reaction for 5 hours. After the reaction was completed, toluene (300.0 g) was added to the reactor, and dibenzothiophene having chloromethyl introduced thereinto was layer-separated as an intermediate product. The intermediate product layer was stirred, the inner temperature of the reactor was cooled to 25° C., the stirred reactant was washed and layer-separated by using refined water (200.0 g for each time) three times, and then the intermediate product layer was decolorized by using an activated carbon in order to improve a color of a final target compound. After the decolorization, the decolorized reactant was dehydrated by MgSO$_4$, followed by filtration, and MEHQ (4-Metaoxy Phenol) (0.063 g, 0.00057 mol) which is a polymerization inhibitor was put into the reactant (hereinafter, referred to as a reaction solution 2).

A distilled water (200.0 g) was put into another 1 L reactor and an inner temperature of the reactor was cooled to 5° C. The inner temperature of the reactor was maintained at 15° C. or less, and 90% KOH (60.9 g, 0.977 mol) was slowly put into the reactor. After 90% KOH was completely dissolved, the inner temperature of the reactor was maintained to 15° C. or less, and an acrylic acid (78.2 g, 1.085 mol) was slowly put into the reactor. A temperature was raised to a room temperature and TBAB (Tetra-n-butylammonium bromide) (25.3 g, 0.076 mol) was put into the reactor to be dissolved, thereby preparing a KOH/AA aqueous solution.

The prepared KOH/AA aqueous solution was put into the prepared reaction solution 2 and air was injected, followed by a reaction for 4 hours at 80° C. After the reaction was completed, dibenzo[b,d]thiophenylmethyl acrylate was layer-separated as a final target compound, the inner temperature of the reactor was cooled to 25° C., and the reactant was washed and layer-separated by using refined water (200.0 g for each time) three times, followed by decolorization by using the activated carbon in order to improve the color of the final target compound. After the decolorization, the decolorized product was dehydrated by MgSO4, followed by filtration, and MEHQ (4-Metaoxy Phenol) (0.073 g, 0.0006 mol) which is a polymerization inhibitor was put into the reactant. The vacuum distillation device was used to distill toluene, thereby obtaining a mixture of dibenzo[b,d]thiophene-3-ylmethyl acrylate(C) and dibenzo[b,d]thiophene-1-yl methyl acrylate (D) as the final target compound, and a structure of the mixture was confirmed by 1H NMR (C+D=133.4 g, yield of C+D=91.6%. C:D=1:0.7).

1H NMR (400 MHz, CDCl3) of C: δ 5.34 (s, 2H), 5.83-5.86 (dd, 1H), 6.14-6.22 (m, 1H), 6.43-6.49 (dd, 1H), 7.66-7.70 (m, 1H), 7.55-7.60 (m, 2H), 7.85-7.90 (m, 2H), 8.46-8.53 (m, 2H)

1H NMR (400 MHz, CDCl3) of D: δ 5.32 (s, 2H), 5.83-5.86 (dd, 1H), 6.14-6.21 (m, 1H), 6.43-6.49 (dd, 1H), 7.68-7.71 (m, 1H), 7.58-7.60 (m, 2H), 7.84-7.90 (m, 2H), 8.45-8.52 (m, 2H)

Evaluation on the dibenzo[b,d]furanylmethyl acrylate (A+B) of Example 1 and the dibenzo[b,d]thiophenylmethyl acrylate (C+D) of Example 2 in view of physical properties is described as follows, and the physical properties of each acrylate compound prepared by the Example are shown in the following Table 1.

(1) <Viscosity>

Viscosity was measured at 25° C. by using a rotational viscometer (Brookfield, DV-II+ pro).

(2) <Refractive Index>

Refractive index was measured at 25° C. by using a Abbe refractometer (trade name: NAR-1T) of Atago Co., Ltd.

TABLE 1

| Analysis Factor | Di-benzo[b,d]fura-nylmethyl acrylate(A + B) of Example 1 | Di-benzo[b,d]thio-phenylmethyl acrylate(C + D) of Example 2 | Acrylate compound of Related Art | |
|---|---|---|---|---|
| | | | Phenyl-thioethyl acrylate | 2-phenyl-phenoxy ethyl acrylate |
| Appearance | Yellowish liquid | Yellowish liquid | Yellow to pale yellowish liquid | Yellow to pale yellowish liquid |
| Color (APHA) | 151 | 120 | 50 | 50 |
| Viscosity (at 25° C.) | 310.28 cP | 3,304.8 cP | 7~12 (20° C.) | 120.0~150.0 (20° C.) |
| Refractive Index (at 25° C.) | 1.611 | 1.636 | 1.557 (20° C.) | 1.579 (20° C.) |

As shown in the above Table 1, the acrylate compounds of Examples 1 and 2 of the present invention have significantly high refractive index as compared to the acrylate compound of the related art, such that it is expected that in the case in which the acrylate compounds of the present invention are used in an industrial optical lens, an optical lens for a glass material, and the other products for an optical material, and the like, used in an optical film, a camera, a copying machine, a printer, or the like, brightness enhancement effect is significantly excellent.

INDUSTRIAL APPLICABILITY

As set forth above, the novel (meth)acrylate derivative according to the present invention, which is the liquid fluorene methyl (meth)acrylate derivative containing oxygen or sulfur at position 9 in the fluorene structure, has high refractive index and low viscosity, such that flowability and formability thereof may be superior, and the reactivity thereof may be excellent, thereby having advantages in the preparing process. In addition, the (meth)acrylate derivative is prepared by the low cost process to have economic advantages. Further, the novel (meth)acrylate derivative according to the present invention may have excellent transparency at the time of curing, small degree of yellowing even at the time of being exposed by the light in a long period of time, and excellent formability and adhesive property, and may be used in various fields such as the UV curable resin, the film, and the coating fields.

The invention claimed is:

1. A method for preparing a high refractive (meth)acrylate derivative, the method comprising:
 1) preparing a compound represented by the following Chemical Formula b by putting a fluorene derivative represented by the following Chemical Formula a, paraformaldehyde (PFA), and an acid into a first reactor, followed by a reaction;
 2) preparing a KOH/(meth)acrylic acid aqueous solution by putting a KOH aqueous solution and a (meth)acrylic acid represented by the following Chemical Formula c into a second reactor, followed by putting Tetra-n-butylammonium bromide (TBAB) thereinto; and
 3) preparing a (meth)acrylate derivative represented by the following Chemical Formula 1 by an esterification reaction of the compound represented by the following Chemical Formula b, the reaction product of the step 1), with the KOH/(meth)acrylic acid aqueous solution of the step 2):

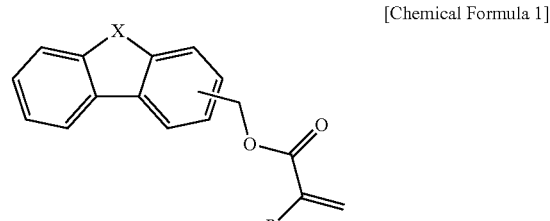

[Chemical Formula 1]

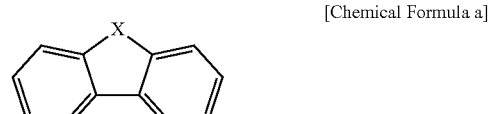

[Chemical Formula a]

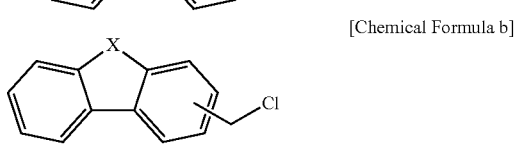

[Chemical Formula b]

[Chemical Formula c]

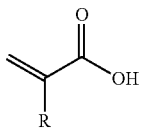

wherein X is O or S, and R is hydrogen or methyl.

2. The method of claim 1, wherein the acid of the step 1) is an acetic acid, a hydrochloric acid, a phosphoric acid, a sulfuric acid, a p-toluenesulfonic acid, or a methanesulfonic acid.

3. The method of claim 1, wherein a reaction temperature of the step 1) is 80 to 85° C.

4. The method of claim 1, wherein in the step 2), the putting of the KOH aqueous solution and the (meth)acrylic acid represented by Chemical Formula c into the second reactor is performed at a temperature of 5 to 15° C., and the putting of Tetra-n-butylammonium bromide (TBAB) thereinto is performed at a temperature of 20 to 30° C.

5. The method of claim 1, wherein the esterification reaction of the step 3) is performed at a temperature of 70 to 90° C.

6. The method of claim 1, further comprising:
additionally putting a polymerization inhibitor into the first reactor after performing the reaction of the step 1), or
additionally putting the polymerization inhibitor after performing the esterification reaction of the step 3),
wherein the polymerization inhibitor is selected from a group consisting of hydroquinone, MEHQ (4-Metaoxy Phenol), ter-tbutylcatechol, p-benzoquinone, phenothiazine, butylated hydroxy toluene, pyrogallol, mono tertbutylhydroquinone, and di-tert-butylhydroquinone.

* * * * *